(12) United States Patent
Sarma et al.

(10) Patent No.: US 11,175,225 B2
(45) Date of Patent: Nov. 16, 2021

(54) COMPOSITION MEASUREMENT SYSTEM

(71) Applicant: Massachusetts Institute of Technology, Cambridge, MA (US)

(72) Inventors: Sanjay E. Sarma, Cambridge, MA (US); Pranay Jain, Delhi (IN)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/280,592

(22) Filed: Feb. 20, 2019

(65) Prior Publication Data
US 2019/0353589 A1 Nov. 21, 2019

Related U.S. Application Data

(60) Provisional application No. 62/632,601, filed on Feb. 20, 2018, provisional application No. 62/807,507, filed on Feb. 19, 2019.

(51) Int. Cl.
| | |
|---|---|
| *G01N 21/47* | (2006.01) |
| *G01N 33/06* | (2006.01) |
| *G01N 33/483* | (2006.01) |
| *G01N 33/49* | (2006.01) |

(52) U.S. Cl.
CPC ......... *G01N 21/4738* (2013.01); *G01N 33/06* (2013.01); *G01N 33/4833* (2013.01); *G01N 33/49* (2013.01); *G01N 2021/4769* (2013.01)

(58) Field of Classification Search
CPC ....... G01N 2021/4769; G01N 21/4738; G01N 33/06; G01N 33/4833; G01N 33/49; G01N 2201/0221; G01N 2201/0635
USPC ................................................ 356/432–448
See application file for complete search history.

(56) References Cited

U.S. PATENT DOCUMENTS

| | | | |
|---|---|---|---|
| 2015/0338351 A1* | 11/2015 | Stockwell | G01N 21/65 356/301 |
| 2016/0097716 A1* | 4/2016 | Gulati | A61B 5/7267 250/339.01 |
| 2016/0231236 A1* | 8/2016 | Gulati | A61B 5/02433 |
| 2017/0131197 A1* | 5/2017 | Jain | H04N 5/213 |
| 2019/0120753 A1* | 4/2019 | Prater | G01N 21/552 |

* cited by examiner

*Primary Examiner* — Tri T Ton
(74) *Attorney, Agent, or Firm* — Occhiuti & Rohlicek LLP

(57) ABSTRACT

A method for measuring one or more quantities characterizing a composition of a medium includes causing a first non-uniform spatially varying optical signal to impinge on a portion of the medium, processing a second optical signal emitted from the medium in response to the first optical signal including determining characteristics of a spatial variation of the second optical signal, and determining the one or more quantities characterizing the composition of the medium based on the characteristics of the spatial variation of the second optical signal.

29 Claims, 15 Drawing Sheets

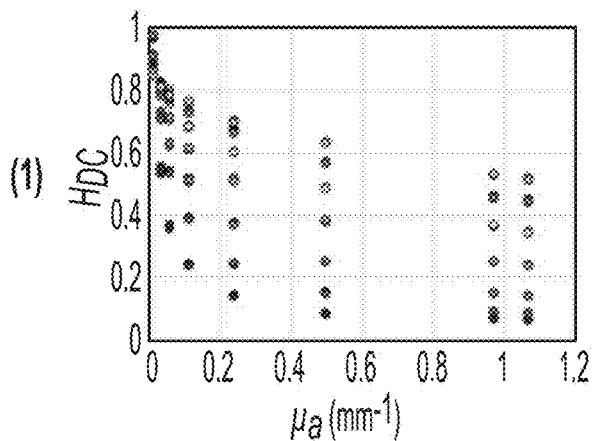
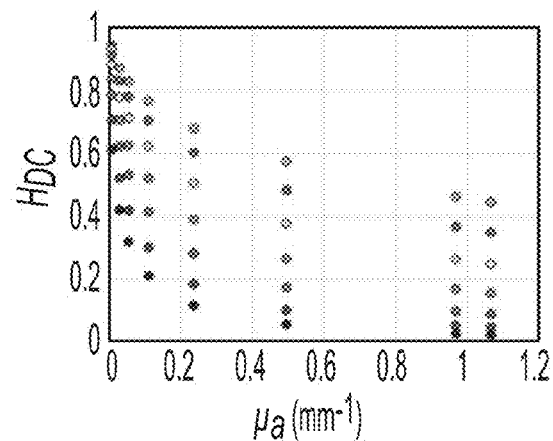
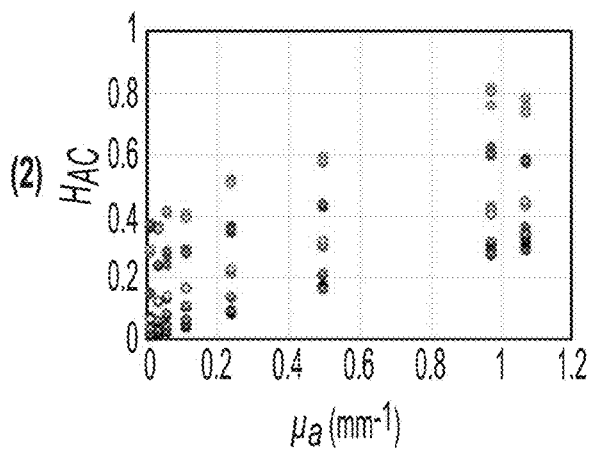
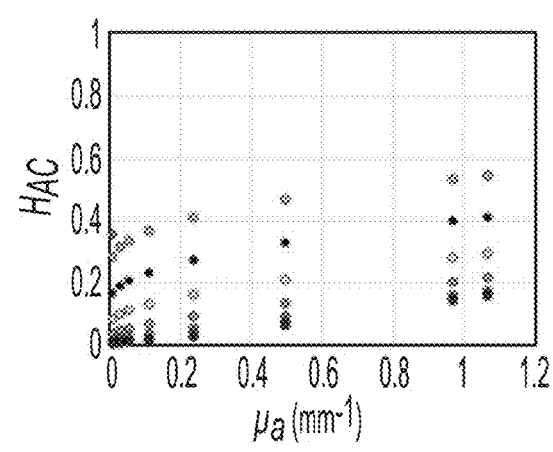
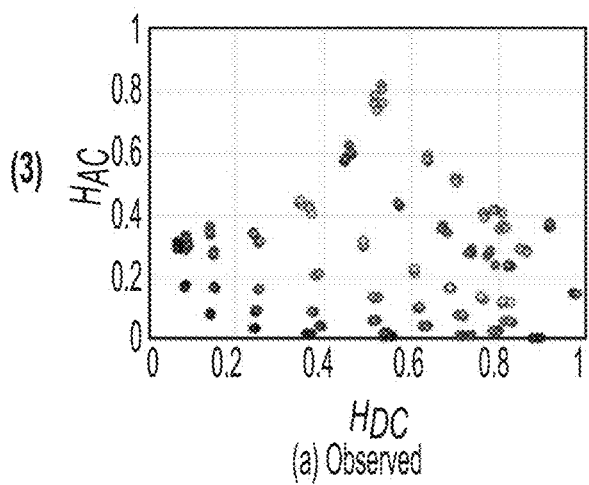
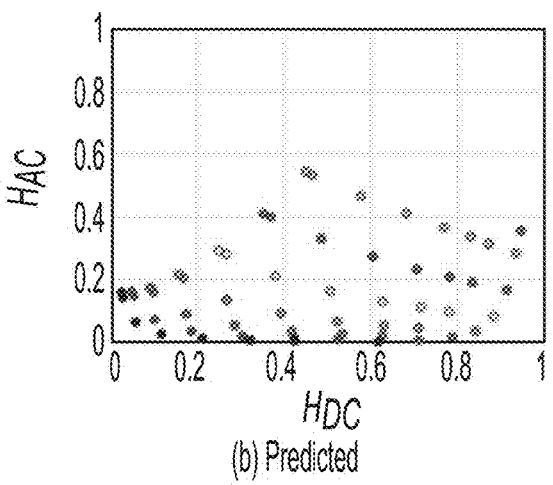
FIG. 9A        FIG. 9B

COMPOSITION MEASUREMENT SYSTEM

CROSS-REFERENCE TO RELATED APPLICATIONS

This application claims the benefit of U.S. Provisional Application No. 62/632,601 filed Feb. 20, 2018 and U.S. Provisional Application No. 62/807,507 filed Feb. 19, 2019, both of which are incorporated herein by reference.

BACKGROUND

This application relates to measurement of a composition, and more particularly to optical measurement of a turbid composition.

Diffuse Optical Imaging (DOI) is a method for non-invasively investigating the optical properties of a material.

There is a need to measure properties of a mixture of one or more liquids and one or more types of particulate matter, such as may be found in milk. Furthermore, there is a need to measure properties of translucent materials such as skin and eye tissue.

SUMMARY

In a general aspect, Diffuse Optical Imaging is used to measure properties of a turbid medium (e.g., mixtures of one or more liquids and one or more types of particulate matter). Optical properties of dense colloidal dispersions like milk, blood, sludge and haze can reveal the particulate composition of these seemingly homogenous systems. These measured properties may be used, for example, in applications such as process control, medical diagnostics, and environment monitoring.

A variety of Diffuse Optical Imaging techniques may be used. Different of these techniques may vary in methods of illumination, observation and signal processing. In some embodiments, Spatial Frequency Domain Imaging is used. A spatially modulated light pattern is projected on a turbid sample as structured illumination and the diffuse backscattered pattern is imaged. Using a system identification approach, the spatial frequency response of the sample is measured and related to the bulk optical properties using light transport models.

In some embodiments, randomly generated patterns (e.g., speckle patterns) are used as structured illumination as opposed to deterministically modulated patterns. Random patterns contain a wide band of spatial frequencies, allowing faster measurement without compromising on measurement reliability. They are also easier to generate and control, reducing system hardware and complexity, allowing for scalable and portable devices.

In another general aspect, the Bulk Optical Properties (BOPs) of turbid media are measured using spatially broadband inputs and digital imaging. Commonly useful BOPs include absorption coefficient, scattering coefficient, anisotropy factor and refractive index. In a primary embodiment, speckle patterns are generated using a coherent light source and a diffusive reflective surface. These patterns are projected on a homogenous turbid medium like milk.

In some examples, digital imaging is used to observe the diffuse backscatter from the medium. The original projected pattern is observed as blurred due to diffusion inside the medium. The original and backscattered patterns are compared as 2D signals in the spatial frequency domain to measure the Spatial Frequency Response of the system. The measured response is then used to estimate the BOPs of the medium. The relation between measured response and BOPs is developed offline using underlying physical scattering models and empirical studies.

In some examples, using spatially broadband projections for the present objective allows for simultaneously estimating the Spatial Frequency Response of the system for a wide range of spatial frequencies without the need to generate multiple discrete frequencies. The advantages of using speckle patterns as spatially broadband projections are several. First, speckle patterns are inherently bandlimited and hence prevent aliasing in digital imaging. Second, generating speckle patterns needs only simple hardware allowing for development of affordable, miniature and handheld instruments. Third, speckle patterns are understood as samples of a stationary random process and generating multiple independent speckle patterns as samples of the same random process is inexpensive and fast. In other examples, other random, pseudo-random or definite broadband spatial light projections may be used instead of speckle patterns. In place of a diffuser for generating speckles, specially designed transmission or reflection diffraction gratings may be used to generate such patterns with either a combination of discrete frequencies or a wide range of frequencies. Alternatively, mirrors of a micro-mirror array may be controlled with a pseudo-random arrangement to generate patterns.

The spatially broadband projection may be at a discrete wavelength of light, or a combination of multiple wavelengths. The measurement may be repeated at multiple wavelengths of light to estimate BOPs over a spectrum. In some examples, a set of coherent laser diodes is used (405 nm for violet light, 532 nm for green, 635 nm for red and 980 nm for deep red) to individually create speckles one at a time. Laser diodes provide for low-cost, miniature and easily controlled sources of coherent light. In other examples, other coherent and incoherent sources of radiation may be used such as LEDs, gas lasers, tunable lasers etc. The wavelengths need not be limited to the visible range and may stretch from UV to Infrared.

Digital Imaging may be used for observing the spatial distribution of backscattered radiation. It allows for a robust, rapid, miniature and low-cost method of observing the system output. The digital image sensor may be coupled with focusing optics, set to focus light from the plane of projection onto the sensor plane. The focusing optics may be achromatic to focus multiple projected wavelengths, or adaptive to provide multiple focus settings. The image sensor in the present embodiment may be placed perpendicular to the projection plane. In other embodiments, the camera may be placed at an angle, or at a distance, with additional imaging optics in the middle. In yet other embodiments, the camera is used in tandem with other image sensors that are spatially separated or have different wavelength sensitivity, focusing optics, and sensor resolutions. Such image sensor systems advantageously improve measurement fidelity, for example, when three-dimensional (3D) mapping a surface using stereoscopy in medical imaging applications. The image sensor systems may be used to remove uncorrelated noise.

In some examples, the system is packaged as a miniature, modular sensing device while preserving the sensing modality and performance. Some aspects, can be used for other turbid media, emulsions and colloids not limited to milk. In yet other embodiments, it can be used to measure BOPs locally in heterogeneous media such as skin tissue.

In a general aspect, a method for measuring one or more quantities characterizing a composition of a medium including a mixture of components including one or more liquids and one or more types of particulate matter includes causing a first non-uniform spatially varying optical signal to impinge on a portion of the medium, processing a second optical signal emitted from the medium in response to the first optical signal, including determining characteristics of a spatial variation of the second optical signal, and determining the one or more quantities characterizing the composition of the medium based on the characteristics of the spatial variation of the second optical signal.

Aspects may include one or more of the following features.

The first non-uniform spatially varying optical signal may include a speckled optical pattern. Causing the first non-uniform spatially varying optical signal to impinge on the portion of the medium may include causing a light source to direct a beam of light through an optical diffuser or toward a diffusive reflector to form the first non-uniform spatially varying optical signal. The method may include causing a translation and/or a rotation of the optical diffuser relative to the light source. The light source may include a laser light source. More generally, other patterns with known or statistically expected spatial frequency characteristics may be used instead of the speckled pattern.

The first non-uniform spatially varying optical signal may include a plurality of randomly distributed optical components (e.g., spatial frequency components). The method may include causing a sensor to sense the second optical signal, wherein sensing the second optical signal includes capturing one or more two-dimensional images of the second optical signal. The sensor may include a camera. The characteristics of the spatial variation of the second optical signal may include spatial frequency data characterizing the spatial variation of the second optical signal. Determining the spatial frequency data may include transforming the second optical signal from the spatial domain to the frequency domain.

Determining the one or more quantities characterizing the composition of the medium may include comparing the characteristics of the spatial variation of the second optical signal to a plurality of predetermined characteristics of spatial variation of optical signals, each predetermined characteristic of spatial variation of an optical signal being associated with a corresponding set of one or more quantities, to select a first predetermined characteristic of spatial variation of an optical signal and identifying the set of one or more quantities associated with the first predetermined characteristic of spatial variation of an optical signal as the one or more quantities characterizing the composition of the medium.

Determining the one or more quantities characterizing the composition of the medium may include processing the characteristics of the spatial variation of the second optical signal using a machine learning algorithm. The machine learning algorithm may include a neural network. Determining the one or more quantities characterizing the composition of the medium may include determining the set of one or more quantities based on a fitting of an optical model of the medium to the characteristics of the spatial variation of the second optical signal.

The process may be repeated in multiple iterations, with a different spatially-varying optical signal being used on each iteration. These signals may represent different random instances from a distribution of spatial variation.

The one or more quantities characterizing the composition of the medium may be relative (e.g., proportions, density) or absolute (e.g., amount) quantities characterizing the mixture of components. The medium may be a colloid. The colloid may be milk. The one or more types of particulate matter may include milk fat and milk protein.

In another general aspect, a method for measuring one or more quantities characterizing a turbid medium includes causing a first non-uniform spatially varying optical signal to impinge on a portion of the medium, processing a second optical signal emitted from the medium in response to the first optical signal, including determining characteristics of a spatial variation of the second optical signal, and determining the one or more quantities characterizing the medium based on the characteristics of the spatial variation of the second optical signal.

Aspects may include one or more of the following features.

The one or more quantities characterizing the turbid medium may include bulk optical properties of the turbid medium. The method may include using the bulk optical properties of the turbid medium to characterize a composition of the turbid medium. The turbid medium may include blood.

In another general aspect, a method for measuring one or more quantities characterizing a translucent medium includes causing a first non-uniform spatially varying optical signal to impinge on a portion of the medium, processing a second optical signal emitted from the medium in response to the first optical signal, including determining characteristics of a spatial variation of the second optical signal, and determining the one or more quantities characterizing the medium based on the characteristics of the spatial variation of the second optical signal.

Aspects may include one or more of the following features.

The translucent medium may be a biological tissue. The biological tissue may be eye tissue. The biological tissue may be skin tissue.

Among other advantages, using a speckle pattern rather than an impulse requires less sensor dynamic range and better utilizes the dynamic range of the sensor.

Other features and advantages of the invention are apparent from the following description, and from the claims.

DESCRIPTION OF DRAWINGS

FIG. 9A shows a mapping of two parameters ($H_{AC}$, $H_{DC}$) to an absorption coefficient ($\mu_a$).

FIG. 9B shows a mapping of two parameters ($H_{AC}$, $H_{DC}$) to a scattering coefficient ($\mu_s$).

DESCRIPTION

Figure 1:
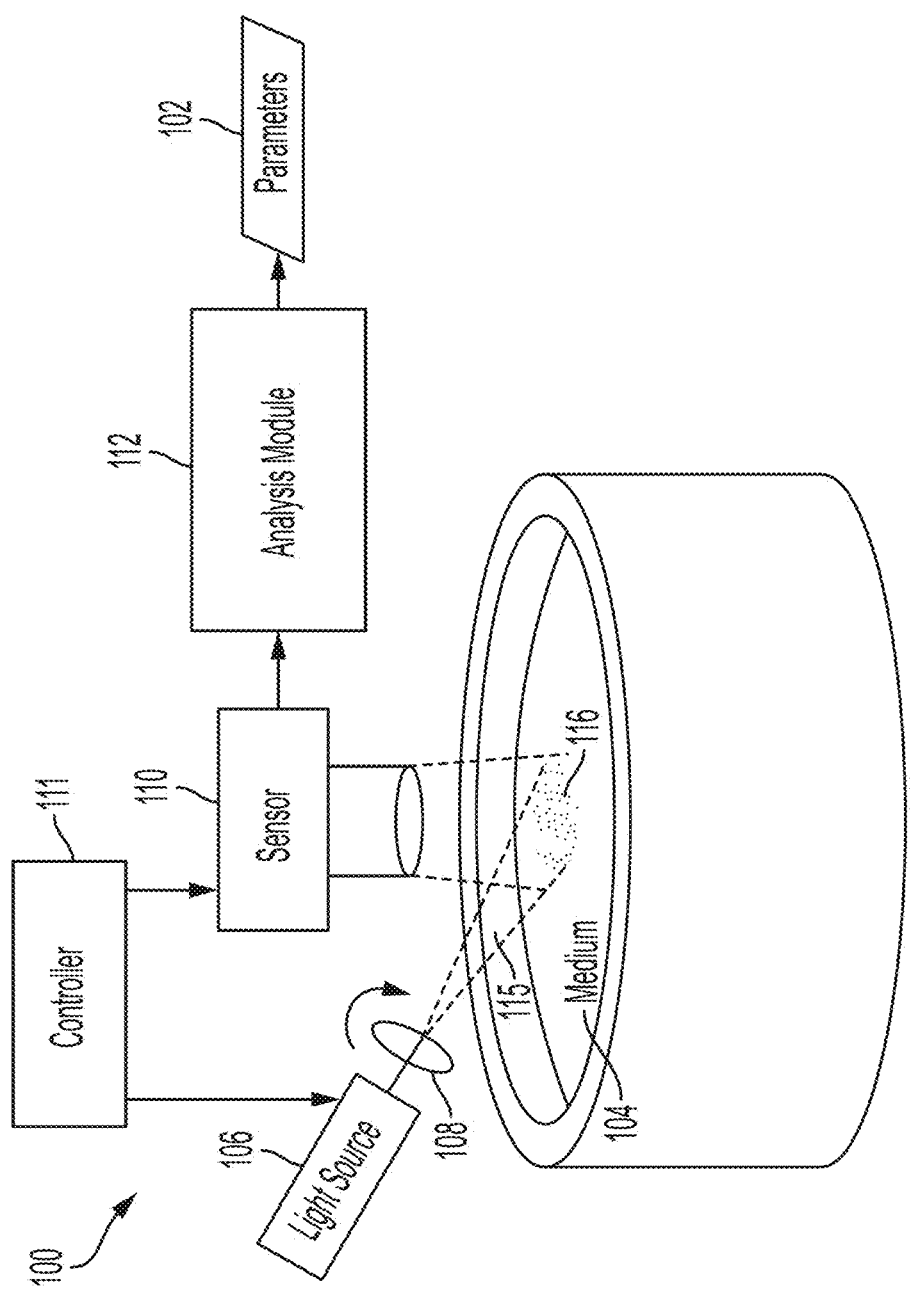
FIG. 1 is a block diagram of a system for measuring one or more quantities related to a composition of a medium including a mixture of one or more liquids and one or more types of particulate matter.

Referring to FIG. 1, a measurement system 100 is configured to measure one or more parameters 102 (or quantities or proportions) related to a composition of a medium 104. In one exemplary use of the system 100, the medium 104 is milk, which is a colloidal mixture including fats and proteins suspended in a liquid. In such an example, the system 100 may be configured to measure quantities or proportions of the quantities that characterize the amount of fats and proteins present in the milk.

In a process which may be iterated multiple times, the system 100 includes a light source 106 (e.g., a laser or light emitting diode), an optical diffuser 108, a sensor 110, an analysis module 112, and a controller 111. In operation, the controller 111 causes the light source 106 to emit a beam of light 114 (e.g., a laser beam) which travels through the optical diffuser 108. After passing through the optical diffuser 108, the light forms a spatially-varying optical pattern (e.g., a pseudo-random speckle or dot pattern or a random binary pattern) 115, generally including a number of randomly arranged dots (or other shapes) of light, on the medium 104. In some examples, the optical diffuser 108 rotates and/or translates relative to the light source 106 such that the speckled pattern 116 projected on the medium 104 varies over time.

The optical pattern 115 impinges on the medium 104 and at the surface and near subsurface interacts (e.g., reflects, diffuses, etc.) with the medium causing a resulting specked pattern 116 to be emitted from the medium. This signal 116 also has spatially-varying characteristics, which depend not only on the characteristics of the signal 115 but also on the characteristics of the medium. The controller 111 causes a sensor 110 (e.g., a camera) to capture sensor data including one or more spatial representations (e.g., 2D images) of the speckled pattern 116 that is incident on the medium 104 and provides the sensor data to the analysis module 112, which computes the parameters 102 (e.g. the quantities that characterize the amount of fats and proteins present in the milk). In some examples, multiple of the one or more spatial representations, which vary over time, are averaged or otherwise combined to form the sensor data that is provided to the analysis module 112.

Figure 2:
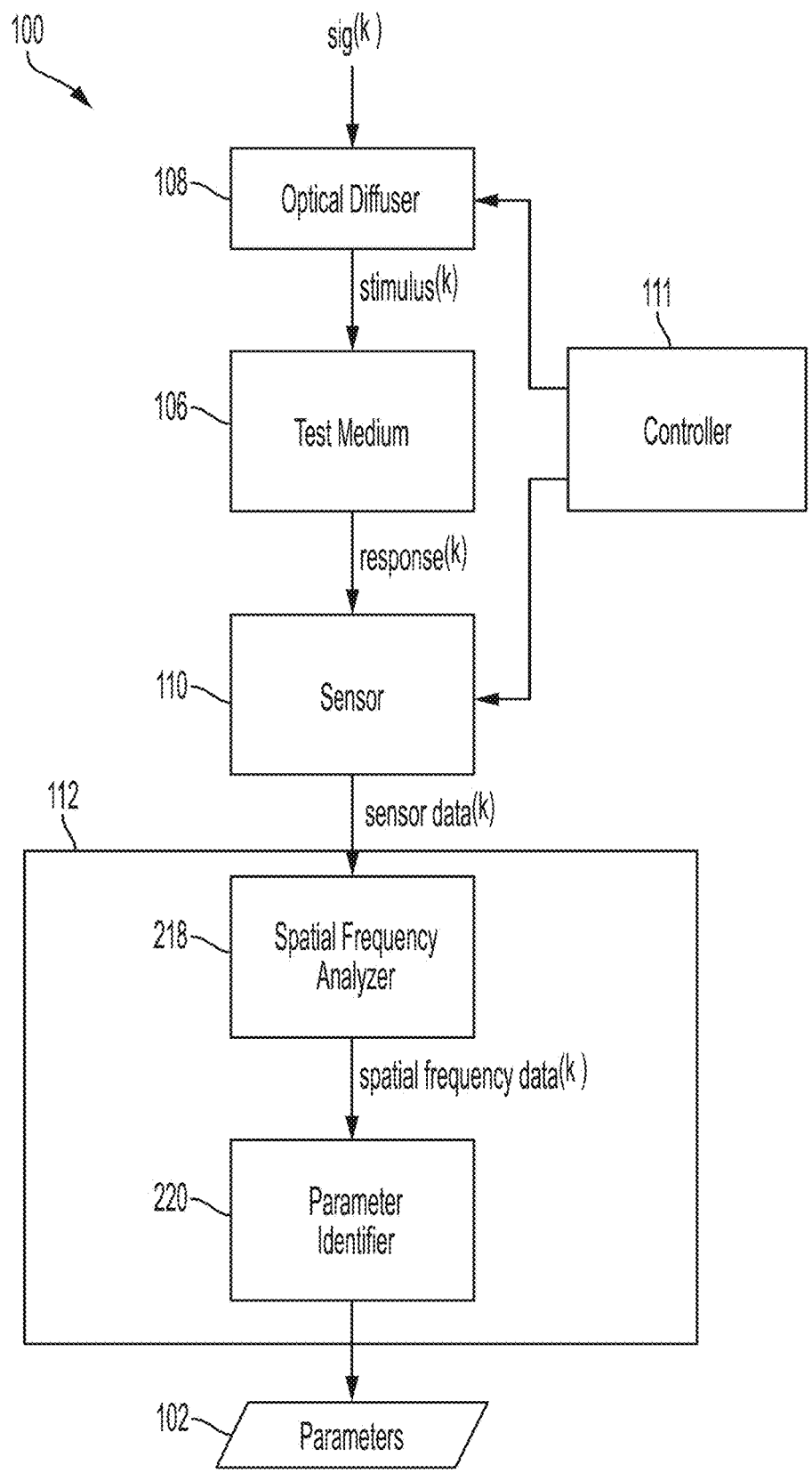
FIG. 2 is a block diagram illustrating steps for measuring one or more quantities related to a composition of a medium including a mixture of one or more liquids and one or more types of particulate matter.

Referring to FIG. 2, in some examples, the analysis module 112 includes a spectral frequency analyzer 218 and a parameter identifier 220. The sensor data is provided to the spatial frequency analyzer 218 which performs one or more signal/image processing operations (e.g., a discrete Fourier transform) to transform the sensor data from a spatial representation to a representation characterizing a spatial variation of the sensor data (e.g., a spectral frequency representation).

The spectral frequency representation is provided to the parameter identifier 220, which processes the spectral frequency representation to determine the parameters. In general, the spectral frequency representation varies according to the parameters 102 (quantities or proportions) related to the composition of the medium 104 (e.g., the quantities that characterize the amount of fats and proteins present in the milk).

In some examples, the parameter identifier 220 utilizes a predetermined model that maps spectral frequency representations of sensor data to parameter values 102. In some examples, the parameter identifier 220 includes a lookup table that includes mappings between empirically determined spectral frequency representations and corresponding parameter values. The spectral frequency representation of the sensor data generated by the spectral frequency analyzer 218 is compared to the spectral frequency representations in the lookup table to determine which one it most closely matches. The parameter values corresponding to the most closely matching spectral frequency representation in the lookup table are returned by the parameter identifier 220 as the parameters 102.

In some examples, the parameter identifier 220 includes a machine learning algorithm (e.g., a neural network) that has been trained to determine parameter values based on spectral frequency representations.

In some examples, the system 100 is implemented as a handheld apparatus. While the above example is described as a system for testing milk, the method and apparatus can also be applied to any type of solution, emulsion, suspension, or colloid.

In some examples, the sensor 110 senses a backscatter (sometimes referred to as a reflection, which should not be interpreted as a specular reflection) of light impinging on the medium 104. In some examples, the sensor 110 senses light that passes through the medium 104.

In some examples, portions of the system 100 are executed in software on a microcontroller or general-purpose computer. In general, the system includes a specific configuration of transducers and sensors and the algorithms and operations performed by the system are a direct consequence of that specific configuration.

In some examples, the analysis module 112 uses a system identification technique to compare input and output images to evaluate an unknown system response. In one embodiment, the analysis module 112 makes use of a spatial frequency distribution of the received image. An image can be considered to be a signal in two dimensions with a non-zero mean shift. The spatial frequency content of an image is observed by calculating its Power Spectral Density (PSD). The input and output PSDs are compared (e.g., divided) to obtain the spatial frequency response of the system. In this embodiment, the spatial frequency response is used to characterize the medium being sensed. In another embodiment, a forward convolution approach is used to evaluate the unknown system response. More generally, any suitable system identification technique can be used to evaluate the unknown system response.

Figure 3A:
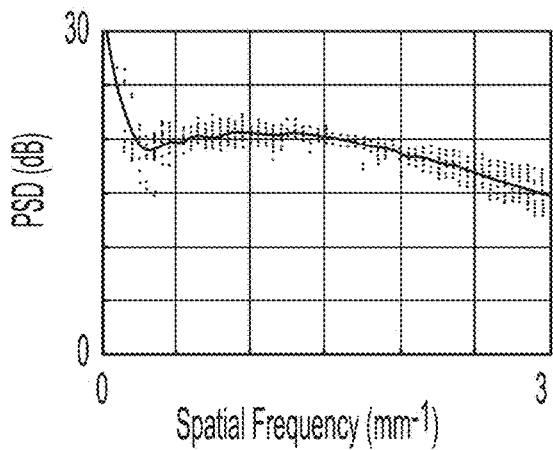
FIGS. 3A-B are plots of power spectral density (PSD) for input and output signals, respectively.
Figure 3B:
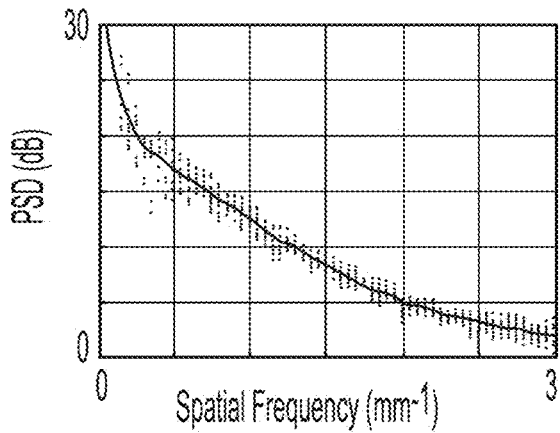
Figure 3C:
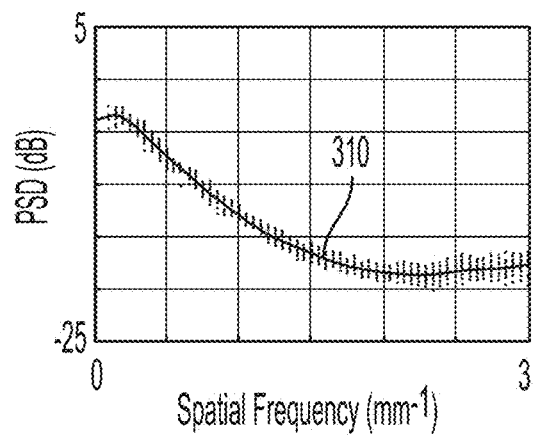
FIG. 3C is a plot of spatial frequency response.
Figure 4:
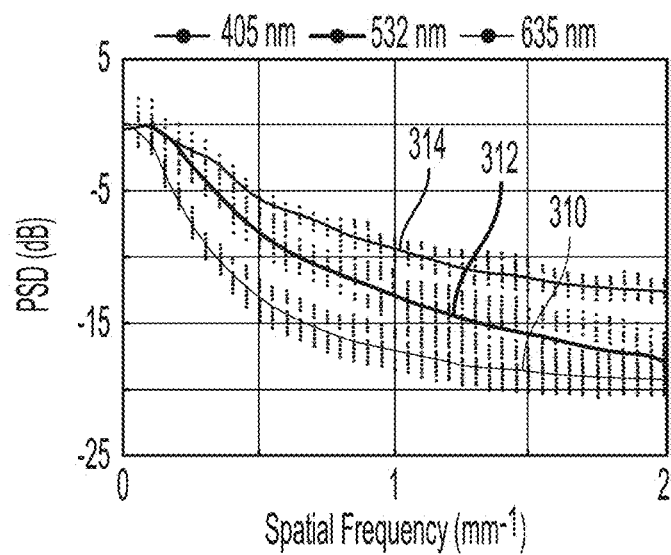
FIG. 4 is a plot of spatial frequency response for three optical wavelengths.

Referring to FIG. 3A, a sample of the input PSD is shown as a function of spatial frequency, while FIG. 3B shows the output PSD for the corresponding input. FIG. 3C shows the spatial frequency response, as well as the spatially moving averaged frequency response 310. This example is for a 405 nm wavelength violet light source. In this example, there are three separate light sources, 405 nm for violet light, 532 nm for green. 635 nm for red, resulting in three frequency responses 310, 312, and 314, respectively, as shown in FIG. 4.

One approach to characterizing the spatial frequency response is according to a low frequency attenuation (PSD loss) and a high frequency attenuation. For example, the low frequency attenuation may be associated with light absorption in the medium, while the high frequency attenuation may be associated with scattering in the medium. The low and high frequency attenuation may be measured at predetermined frequencies. Alternatively, a regression approach may be used in which a parameterized spatial frequency response is fitted to the measured data, and the low and high spatial frequency attenuation is determined from the regression model.

Figure 5:
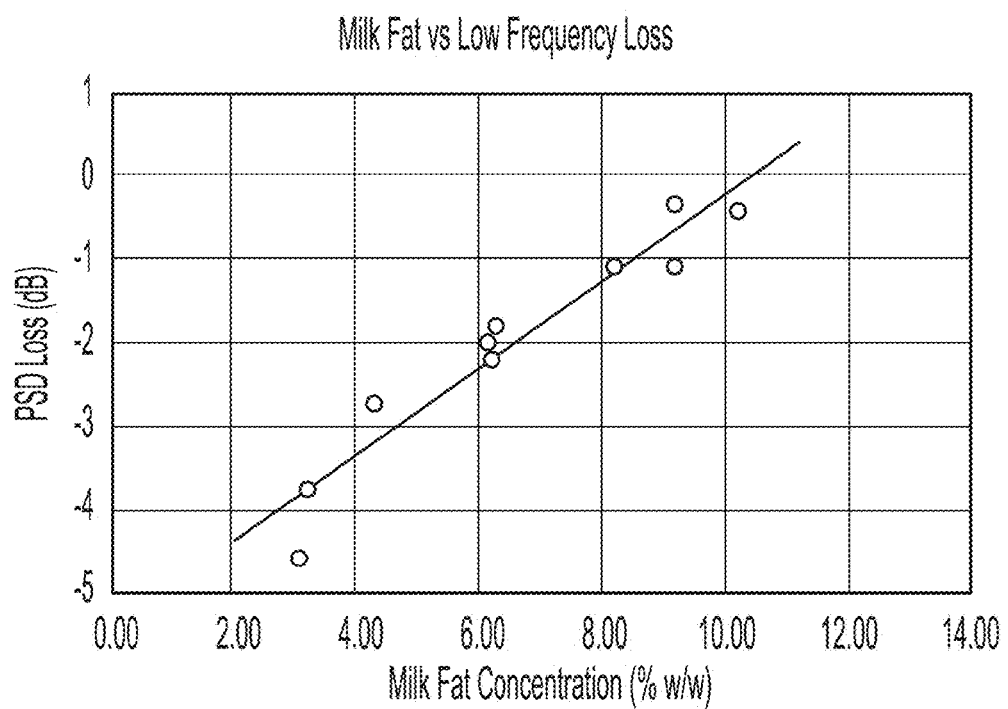
FIG. 5 is a plot of attenuation versus milk fat concentration.
Figure 6:
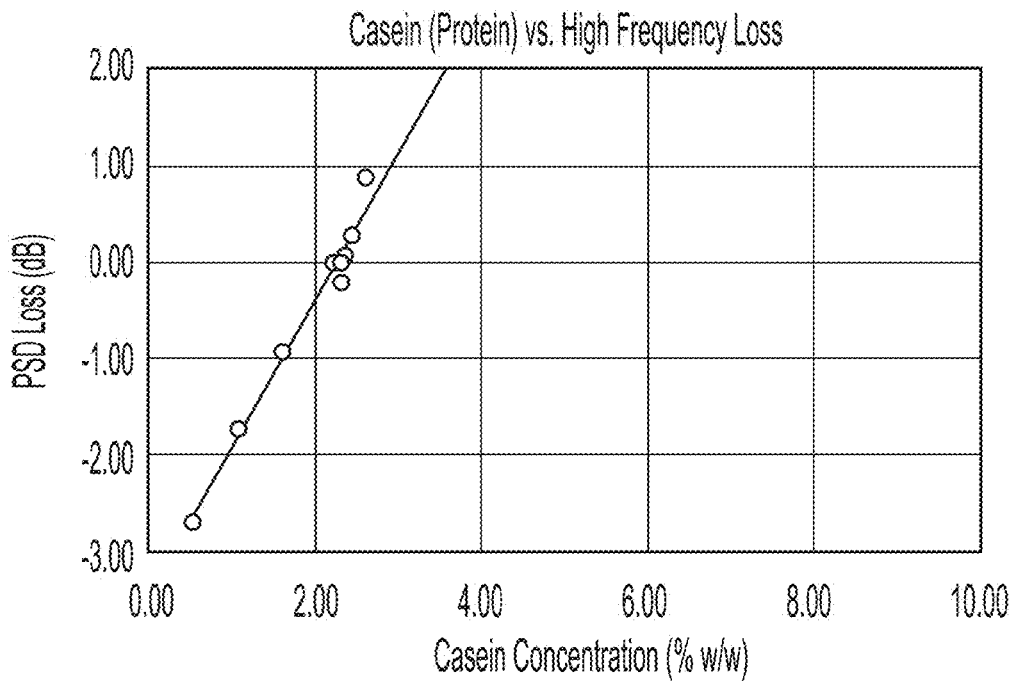
FIG. 6 is a plot of attenuation versus casein concentration.

Referring to FIG. 5, experimental data shows that low spatial frequency attenuation may be used to predict milk fat content, with lesser attenuation (algebraically smaller loss in dB) being associated with lower milk fat content. FIG. 6 shows that high spatial frequency attenuation may be used to predict casein concentration, with lesser attenuation being associated with lower casein concentration.

Figure 7:
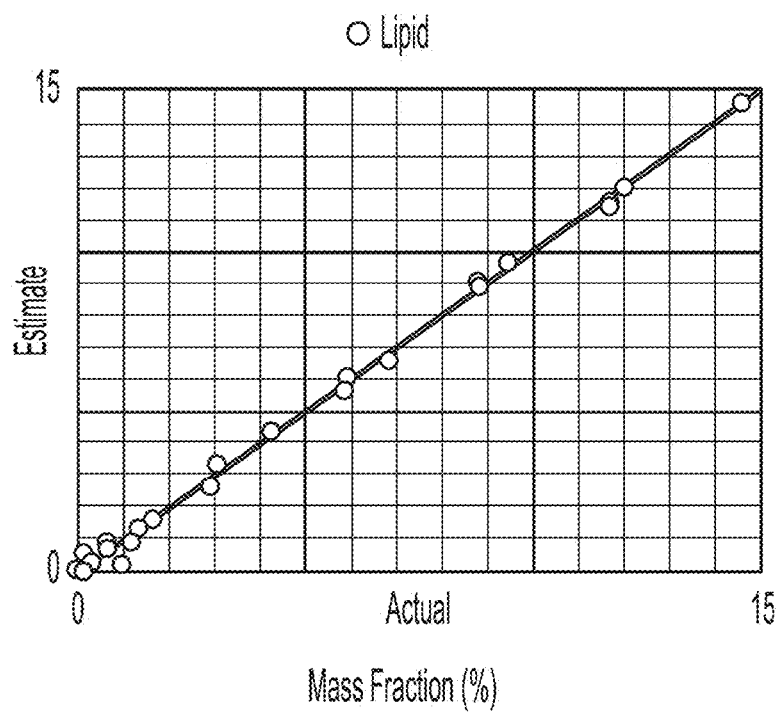
FIG. 7 is a plot of estimated percentage of lipid concentration vs. actual percentage of lipid concentration.
Figure 8:
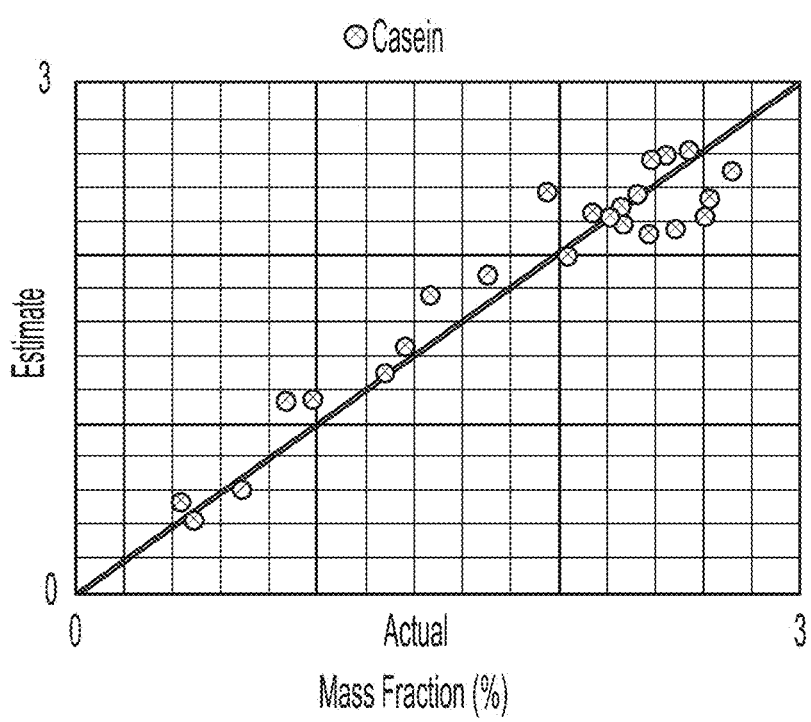
FIG. 8 is a plot of estimated percentage of casein concentration vs. actual percentage of casein concentration.

Referring to FIGS. 7 and 8, in other embodiments, linear or non-linear regression or machine learning based methods are used to characterize the spatial frequency response. In FIGS. 7 and 8, the response over a discrete set of spatial frequencies, for multiple light wavelengths, is tested on a diverse set of milk samples and is processed using regression methods to reduce the multiple data inputs to two independent parameters corresponding to milk fat (lipid) and protein (casein) percentage concentrations. The error in the estimate, compared to reference measurements, is approximately 0.2% for each parameter.

Referring to FIGS. 9A and 9B, the spatial frequency response at a single light wavelength is reduced to an AC and DC component, represented as two parameters: $H_{DC}$ and $H_{AC}$. The two parameters are evaluated for 57 turbid samples with distinct BOPs. FIGS. 9A and 9B shows that the two parameters map to a unique pair of absorption coefficient ($\mu_a$) and scattering coefficient ($\mu_s$). Each dot represents a measurement. Dots with the same colors have the same scattering coefficient. The plots of FIG. 9A (on the left hand side) are as measured from actual data, and the plots of FIG. 9B (on the right hand side) are as predicted from theory. The two differ on scale, but can be easily corrected using calibration.

Figure 10:
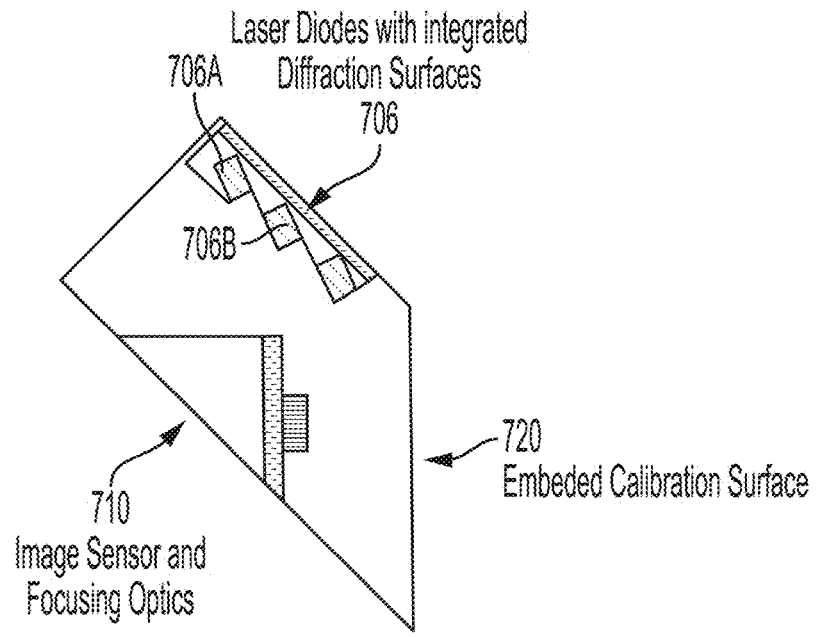
FIG. 10 is cross-section of a sensor module.
Figure 11:
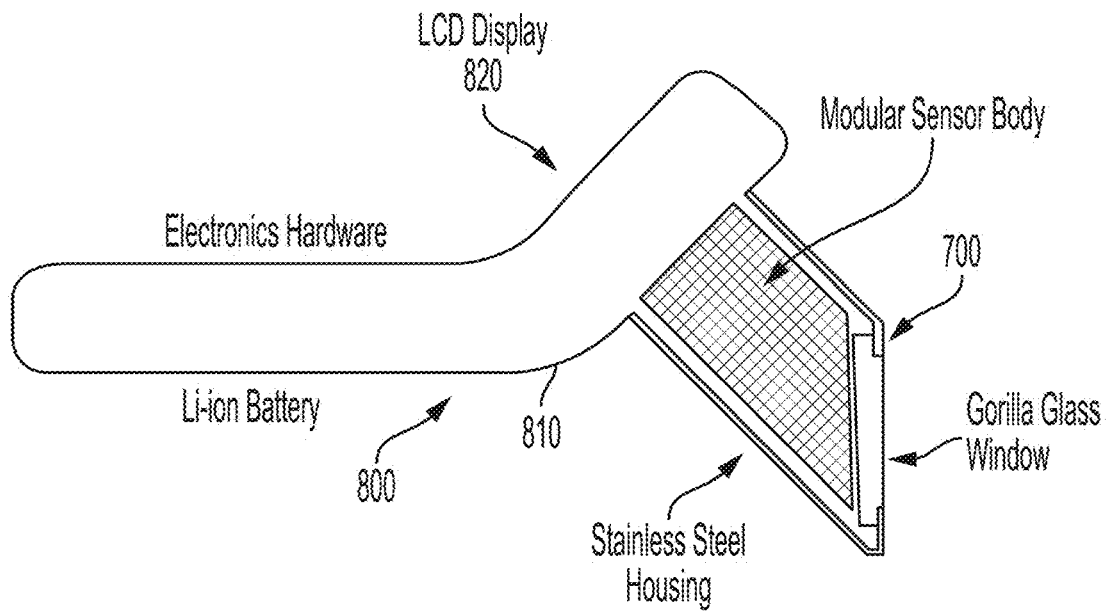
FIG. 11 is a cross-section of a handheld instrument.
Figure 12:
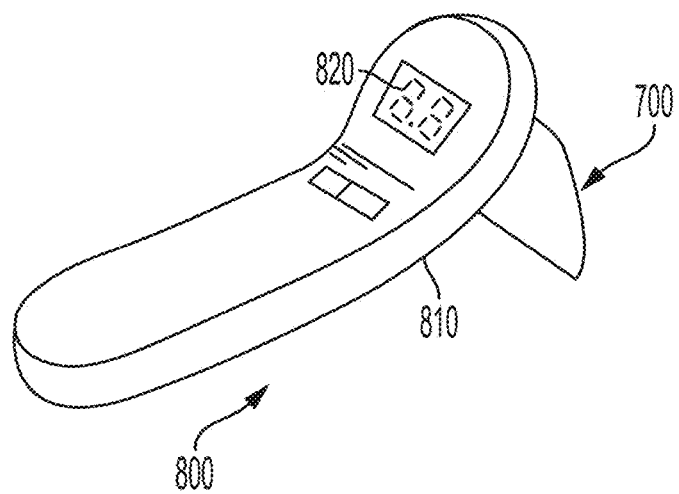
FIG. 12 is a perspective view of the instrument of FIG. 8.
Figure 13:
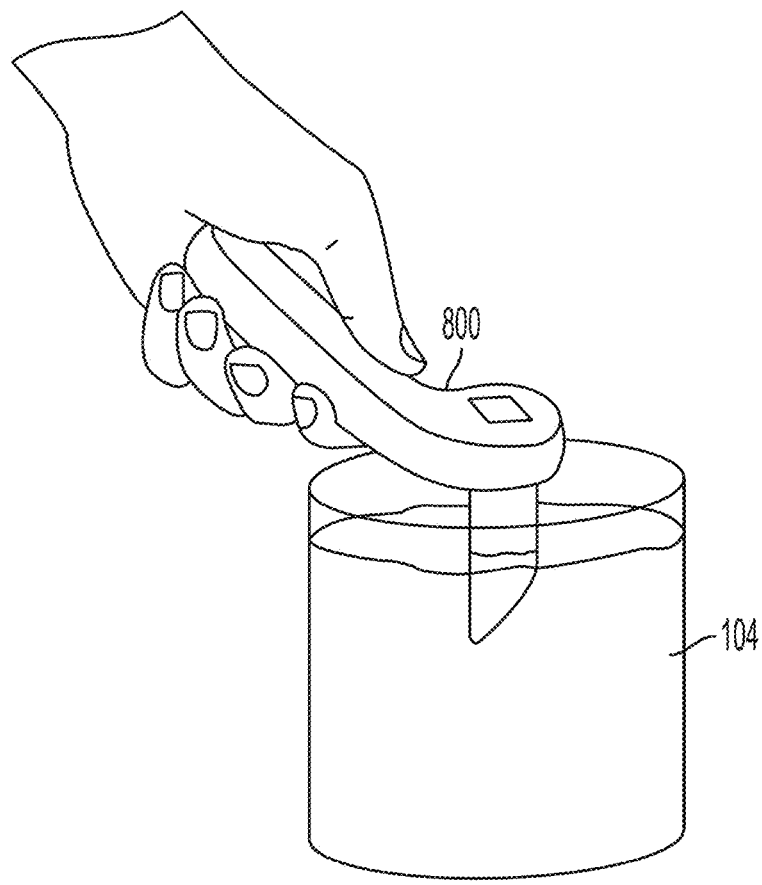
FIG. 13 is a perspective view of the instrument of FIGS. 8-9 in use.

An embodiment of an integrated milk sensor is shown in FIGS. 10-13. Referring to FIG. 10, a sensor module 700 includes a laser diode module 706, including three separate laser diodes 706A-C, each including a diffusion surface, and an image sensor 710, which includes requisite focusing optics. Referring to FIG. 11, the sensor module 700 is integrated in a handheld instrument 800, which includes a handled 810 holding a battery, and display 810, for presenting results to a user of the instrument. FIG. 12 shows a perspective view of the instrument, and FIG. 13 shows the instrument in a typical use measuring properties of a medium 104 (i.e., milk).

In the embodiment of the sensor module 700, there is not necessarily a mechanism for varying the speckle pattern, with diffusing surfaces being integrated into the laser diodes 706A-C. A number of alternative embodiments are described below with reference to FIGS. 14-18.

Figure 14:
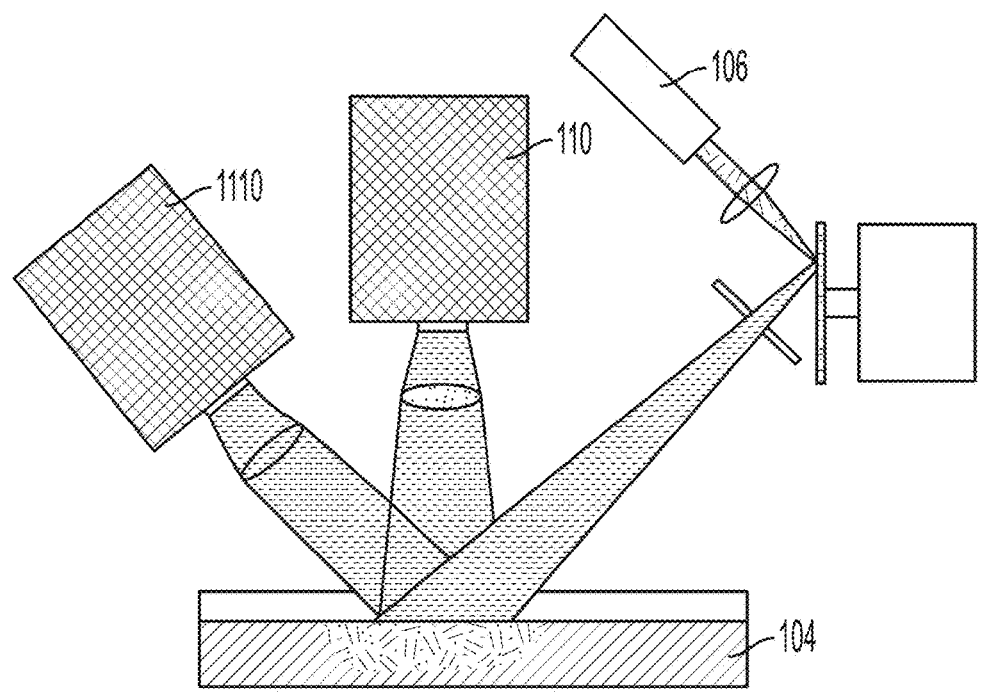
FIGS. 14-15 are block diagrams of alternative embodiments.

In some embodiments, the instruction includes a sensor that measures the power spectrum of the input rather than using an assumed or predetermined power spectrum (e.g., from a previous calibration). Referring to FIG. 14, in some embodiments the instrument includes a sensor 1110 that receives a backscatter of the input speckle pattern off the surface (e.g., an interface between a glass laser and air or the medium being sensed), and a sensor 110 that receives the backscatter/diffusion from the medium. This arrangement permits simultaneous measurement of the input and output PSD, which in turn permits determination of the spatial frequency attenuation.

Figure 15:
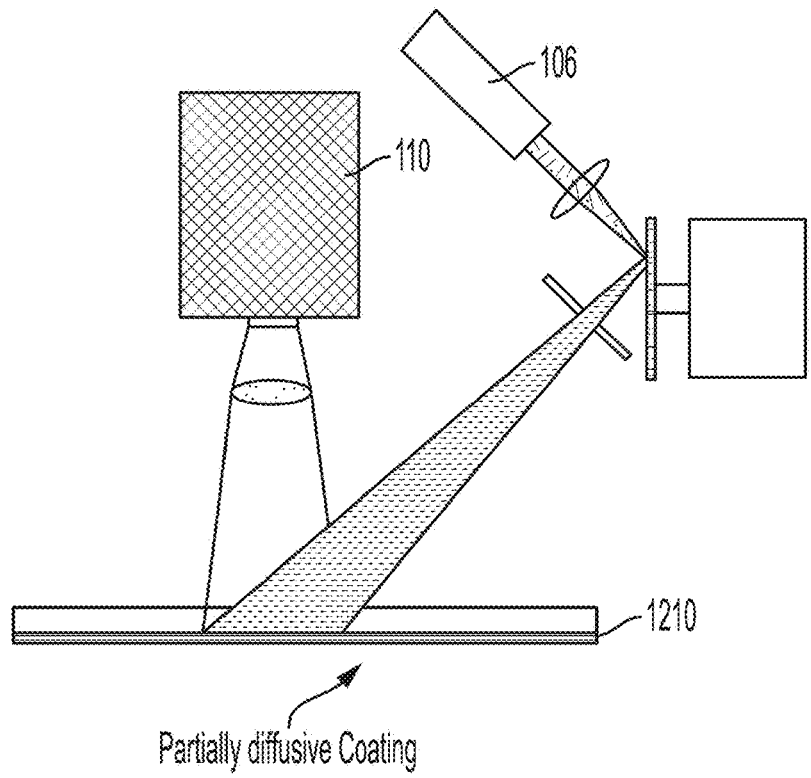

Referring to FIG. 15, another alternative embodiment has a glass window 1210 that is coated with a partially diffusive coating. The diffusive coating allows the same sensor 110 to observe and estimate the input speckle PSD when no sample is in place (e.g., before submersion in milk), and then to observe and estimate the output speckle PSD during measurement. The reflectance from the coating can be subtracted from in-sample measurements using image and signal processing techniques.

Figure 16A:
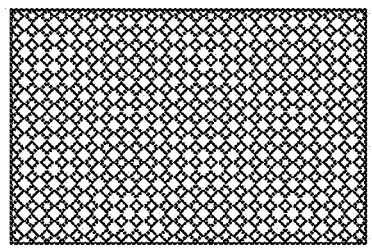
FIGS. 16A-B are diagrams of diffuser windows.
Figure 16B:
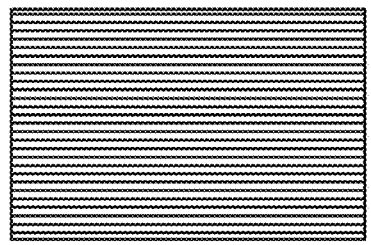

Referring to FIGS. 16A-B, in another embodiment the glass window has opaque diffusers in specific regions of the window. This allows for true simultaneous measurement of input and output speckle patterns. The opaque diffusers may be distributed in fixed patterns, as illustrated in FIGS. 16A-B. As the location of the diffusers is fixed with respect to the camera, the observed image can be separated into input and output images, and the power spectral density can be independently estimated.

Figure 17:
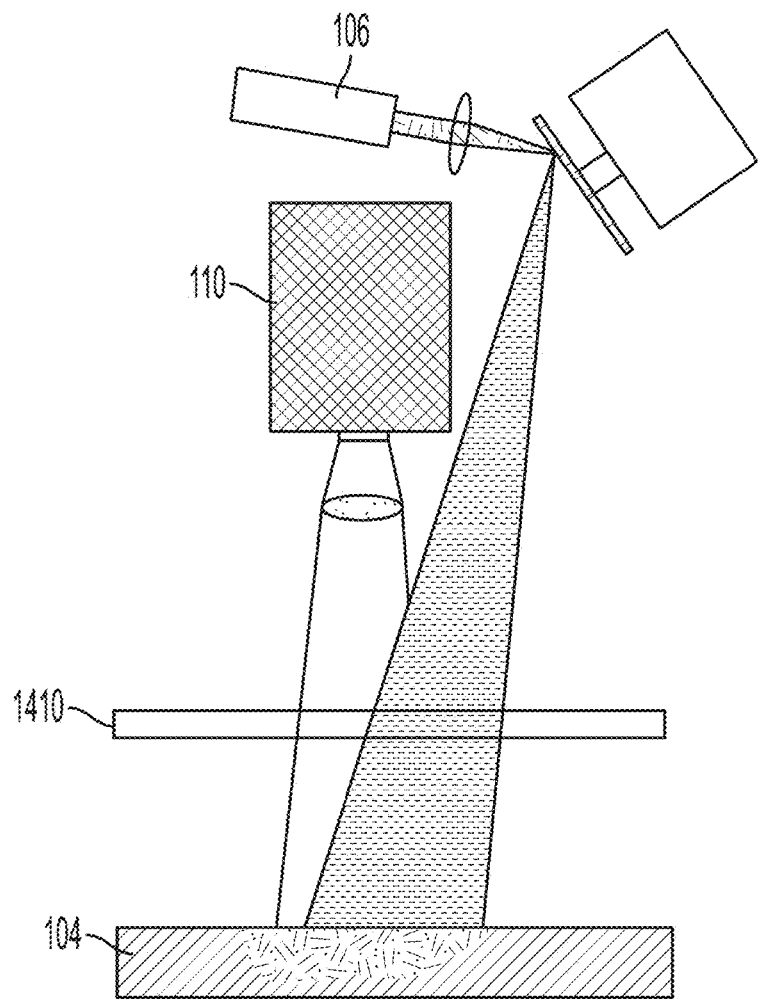
FIG. 17 is a block diagram of an alternative embodiment.
Figure 18:
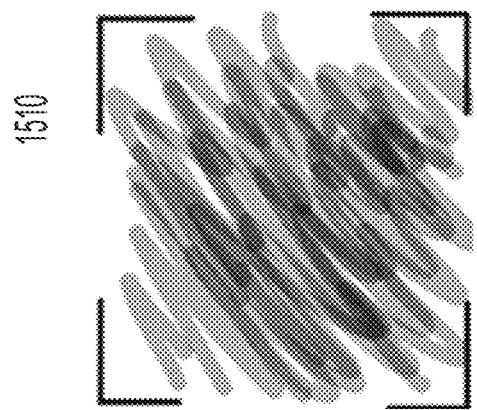
FIG. 18 includes a cross-sectional view of an alternative non-contact embodiment, and a projection pattern used by the instrument.
Figure 18:
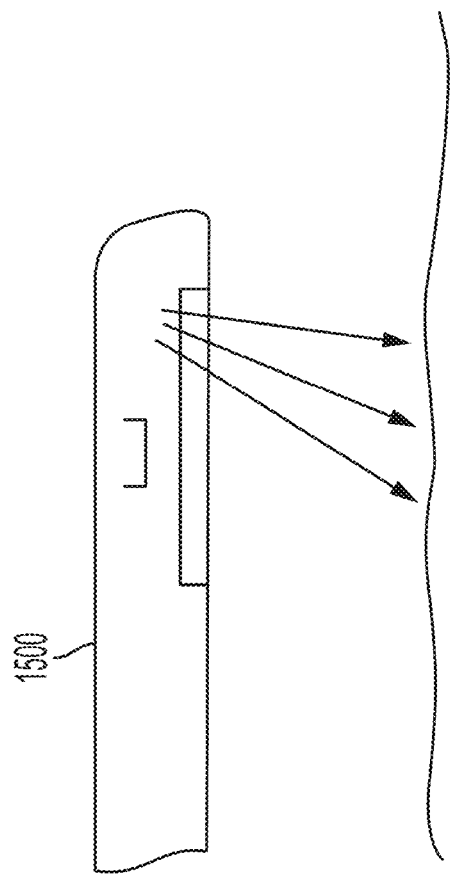

Referring to FIG. 17, yet another embodiment makes use of a non-contact approach. In this embodiment, the sample medium 104 is separated from a window 1410. Speckles, like other spatially distributed diffraction patterns, expands with distance from diffuse surface without loss of spectral quality. If the sample is at a distance from the sampling window, the speckles can still be used to perform the measurements described as described above. Referring to FIG. 18, to assist in correcting for the distance and surface undulations, the instrument 1500 may project a fixed laser pattern 1510 as a fiducial to provide a frame to the measurement. The edges of the frame can be detected using image processing algorithms. The fiducial may also double as a visual indication for the operator to know where the instrument is pointing. Ambient light may be rejected from the imaging system using interference filters or other optical means.

Figure 19A:
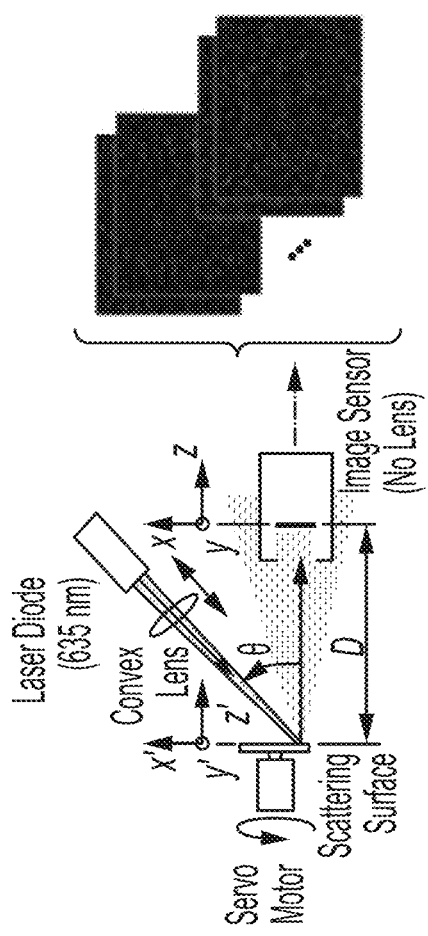
FIG. 19A shows a system configured to direct speckle patterns directly to an image sensor with a rotating scattering surface.

Referring to FIGS. 19A-D, in one embodiment, a system in FIG. 19A is configured to directly observe speckle patterns on an image sensor (without requiring that the speckle pattern reflected from the scattering surface pass through a lens). In this example, the scattering surface is rotated using, for example, a servo motor. A laser is directed through a convex lens onto the scattering surface. The speckle pattern reflected from the scattering surface impinges on the image sensor without passing through any lens.

By rotating the scattering surface (or diffuser) by a small angle, independent speckles representing a random (or pseudo-random) process are generated. Doing so reduces noise. In some examples, the optical system is tuned to project a desired band of spatial frequencies, suited for a particular application.

Figure 19D:
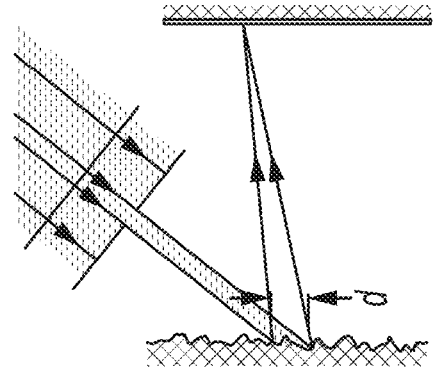
FIG. 19D shows a system configured to direct speckle patterns with a small spot size directly to an image sensor.
Figure 19C:
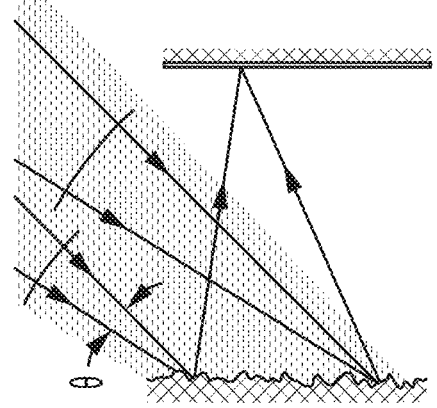
FIG. 19C shows a system configured to direct speckle patterns with a diverging or converging beam directly to an image sensor.
Figure 19B:
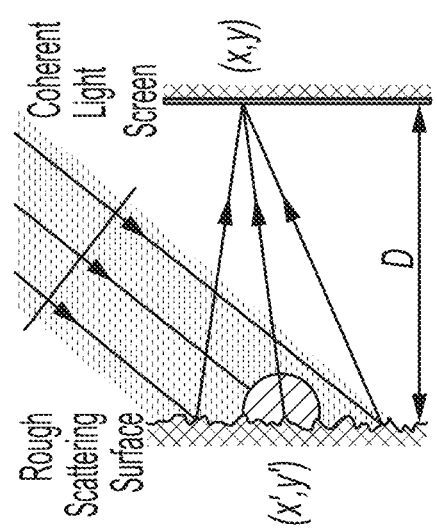
FIG. 19B shows a system configured to direct speckle patterns with a wide spot size directly to an image sensor.

In general, a collimated beam and a wide spot size as in FIG. 19B lead to fully developed speckles, while a converging or diverging beam as in FIG. 19C or a small spot size as in FIG. 19D lead to partially-developed speckles.

Figure 20A:
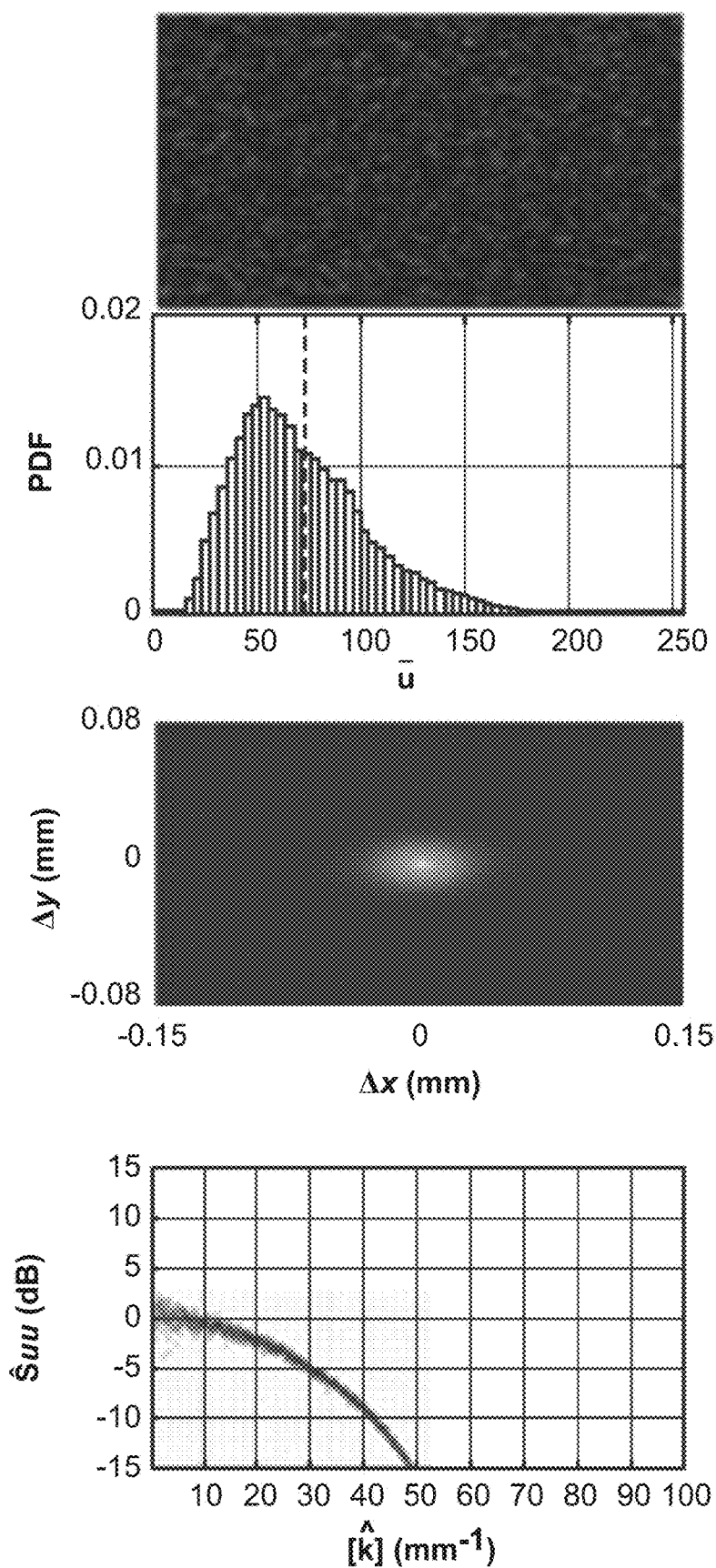
FIG. 20A shows statistics of speckle patterns observed at a first elliptical aperture size.
Figure 20B:
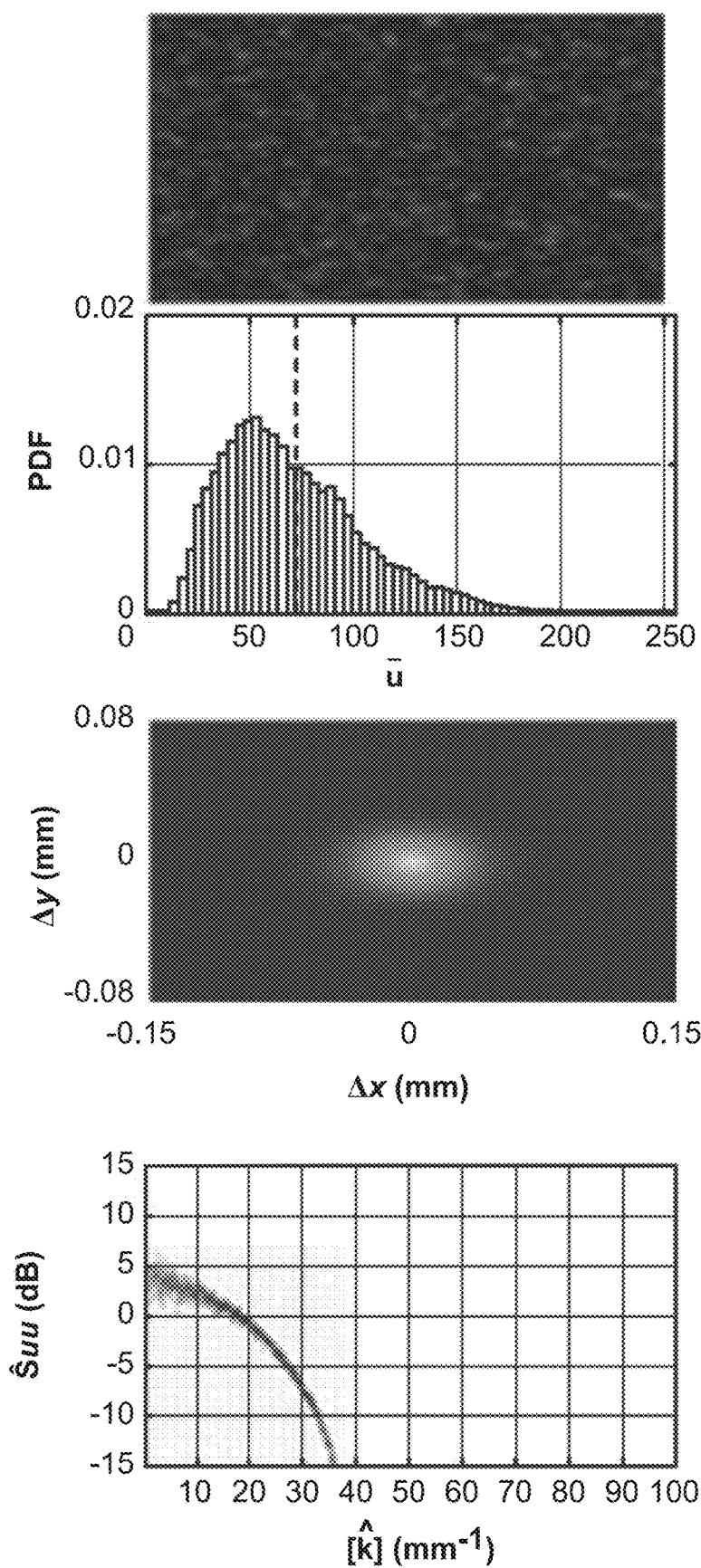
FIG. 20B shows statistics of speckle patterns observed at a second elliptical aperture size.
Figure 20C:
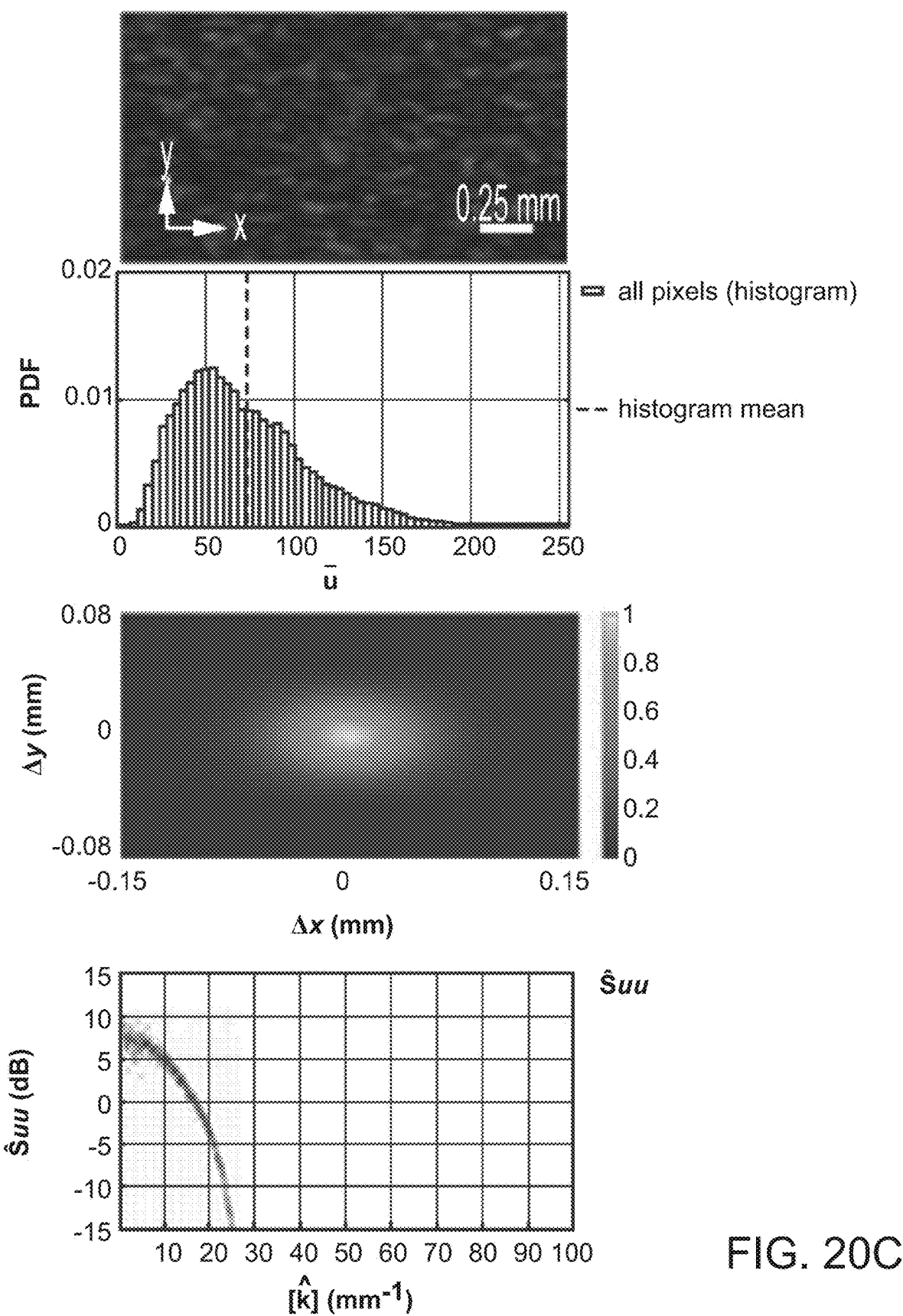
FIG. 20C shows statistics of speckle patterns observed at a third elliptical aperture size.

Referring to FIGS. 20A-C, statistics of speckle patterns observed at three (i.e., columns of images) (FIG. 20A, FIG. 20B, FIG. 20C, respectively) elliptical aperture sizes are shown. The first row of images (1) shows sample speckle images for each elliptical aperture size. The second row of images (2) shows histograms of all pixel readings for each elliptical aperture size. The third row of images (3) shows an estimated ACF $\hat{R}_{UU}(\Delta x, \Delta y)$. The fourth row of images (4) shows an estimated PSD $S_{UU}(0, k_y)$.

In some examples and applications, especially in healthcare, random patterns are generated using digital projectors (micro-mirror devices) or diffraction gratings. These are called 'pseudo random' since the random signal distribution is known. With the random signal distribution known, calibration steps are needed to determine the input PSD or embedded reference measurements.

In some examples, other turbid media (e.g., blood) can be processed using the techniques described herein. For example, a handheld instrument similar to that shown in FIGS. 12-13 may be configured for placement into or adjacent to a sample of blood. The handheld instrument uses the diffuse optical imaging techniques described herein to determine characteristics of the sample of blood. For example, the handheld instrument may determine blood oxygenation and/or concentrations of the various components of blood (e.g., red blood cells, white blood cells, platelets, plasma, etc.).

In other examples, the techniques described herein can be used to determine characteristics of translucent biological tissues such as skin or eye tissue. In such translucent biological tissues, backscatter reveals both surface characteristics of the tissue and sub-surface characteristics of the tissue. For example, the tissue of an eye can be analyzed by the techniques described herein to determine whether the eye tissue is diseased (e.g., for the presence of glaucoma or cataracts). In some examples, the techniques described herein can be used to identify the presence of skin conditions such as melanoma. A device for determining characteristics of translucent biological tissues may include a "wand" that is placed in contact with or adjacent to the tissue. For example, the wand may be pressed against or swept over a patient's skin. A device for analyzing eye tissue may be configured to operate a small distance from a subject's eye to minimize discomfort during operation of the device.

Embodiments of the approaches above may implement the control and image processing procedures in software through execution of instructions (e.g., machine level instructions or higher-level compiled or interpreted programming language instructions) stored on a non-transitory machine-readable medium (e.g., semiconductor memory) by a processor in the device or a processor that is in data communication with the device (e.g., in a personal computing device, such as a "smartphone" in data communication with the instrument. Alternatively, or in addition to software-based processing, some or all of the processing approaches may be implemented in hardware, for example using application-specific integrated circuits (ASICs) or field programmable gate arrays (FPGAs).

It is to be understood that the foregoing description is intended to illustrate and not to limit the scope of the invention, which is defined by the scope of the appended claims. Other embodiments are within the scope of the following claims.

What is claimed is:

1. A method for measuring one or more quantities characterizing a composition of a medium including a mixture of components including one or more liquids and one or more types of particulate matter, the method comprising:
    causing a first non-uniform spatially varying optical signal to impinge on a portion of the medium, the first non-uniform spatially varying optical signal including a randomly distributed spatial intensity pattern;
    processing a second optical signal emitted from the medium in response to the first optical signal, including determining characteristics of a spatial variation of the second optical signal including processing the second optical signal to transform the second optical signal from a spatial representation to a spatial frequency domain representation at one or more spatial frequencies; and
    determining the one or more quantities characterizing the composition of the medium based on the characteristics of the spatial variation of the second optical signal including determining a spatial frequency response of the portion of the medium at the one or more spatial frequencies.

2. The method of claim 1 wherein the first non-uniform spatially varying optical signal includes a speckled optical pattern.

3. The method of claim 1 wherein causing the first non-uniform spatially varying optical signal to impinge on the portion of the medium includes causing a light source to direct a beam of light through an optical diffuser or to reflect off of a diffusive reflector to form the first non-uniform spatially varying optical signal.

4. The method of claim 3 further comprising causing a translation and/or a rotation of the optical diffuser relative to the light source.

5. The method of claim 3 wherein the light source includes a laser light source.

6. The method of claim 1 wherein the first non-uniform spatially varying optical signal includes randomly distributed structured light.

7. The method of claim 6 wherein the randomly distributed structured light includes one or more of dot patterns and micro mirror projections.

8. The method of claim 1 further comprising causing one or more sensors to sense the second optical signal, wherein sensing the second optical signal includes capturing one or more two-dimensional images of the second optical signal.

9. The method of claim 8 wherein the one or more sensors include a camera.

10. The method of claim 1 wherein the characteristics of the spatial variation of the second optical signal include spatial frequency data characterizing the spatial variation of the second optical signal.

11. The method of claim 10 wherein determining the spatial frequency data includes transforming the second optical signal from the spatial domain to the frequency domain.

12. The method of claim 1 wherein determining the one or more quantities characterizing the composition of the medium includes processing the characteristics of the spatial variation of the second optical signal using a machine learning algorithm.

13. The method of claim 12 wherein the machine learning algorithm includes a neural network.

14. The method of claim 1 wherein determining the one or more quantities characterizing the composition of the medium includes determining the set of one or more quantities based on a fitting of an optical model of the medium to the characteristics of the spatial variation of the second optical signal.

15. The method of claim 1 wherein determining the one or more quantities characterizing the composition of the medium includes comparing the characteristics of the spatial variation of the second optical signal to a plurality of predetermined characteristics of spatial variation of optical signals, each predetermined characteristic of spatial variation of an optical signal being associated with a corresponding set of one or more quantities, to select a first predetermined characteristic of spatial variation of an optical signal and identifying the set of one or more quantities associated with the first predetermined characteristic of spatial variation of an optical signal as the one or more quantities characterizing the composition of the medium.

16. The method of claim 1 wherein the one or more quantities characterizing the composition of the medium are proportional quantities.

17. The method of claim 1 wherein the medium is a colloid.

18. The method of claim 17 wherein the colloid is milk.

19. The method of claim 18 wherein the one or more types of particulate matter includes milk fat and milk protein.

20. An apparatus for measuring one or more quantities characterizing a composition of a medium including a mixture of components including one or more liquids and one or more types of particulate matter, the apparatus comprising:
    light source configured to cause a first non-uniform spatially varying optical signal to impinge on a portion of the medium, the first non-uniform spatially varying optical signal including a randomly distributed spatial intensity pattern;
    a sensor for capturing a second optical signal emitted from the medium in response to the first optical signal; and
    an analysis module configured to determine characteristics of a spatial variation of the second optical signal including processing the second optical signal to transform the second optical signal from a spatial representation to a spatial frequency domain representation at one or more spatial frequencies, and to determine the one or more quantities characterizing the composition of the medium based on the characteristics of the spatial variation of the second optical signal including determining a spatial frequency response of the portion of the medium at the one or more spatial frequencies.

21. The apparatus of claim 20 wherein the light source includes a laser source and an optical diffuser on a path from the laser source to the medium, and wherein the analysis module is configured to determine a spatial power spectral density of the second optical signal and to use said power spectral density to determine a spatial frequency response of the medium.

22. A method for measuring one or more quantities characterizing a turbid medium, the method comprising:
    causing a first non-uniform spatially varying optical signal to impinge on a portion of the medium, the first non-uniform spatially varying optical signal including a randomly distributed spatial intensity pattern;
    processing a second optical signal emitted from the medium in response to the first optical signal, including determining characteristics of a spatial variation of the second optical signal including processing the second optical signal to transform the second optical signal from a spatial representation to a spatial frequency domain representation at one or more spatial frequencies; and
    determining the one or more quantities characterizing the medium based on the characteristics of the spatial variation of the second optical signal including determining a spatial frequency response of the portion of the medium at the one or more spatial frequencies.

23. The method of claim 22 wherein the one or more quantities characterizing the turbid medium include bulk optical properties of the turbid medium.

24. The method of claim 23 further comprising using the bulk optical properties of the turbid medium to characterize a composition of the turbid medium.

25. The method of claim 22 wherein the turbid medium includes blood.

26. A method for measuring one or more quantities characterizing a translucent medium, the method comprising:
    causing a first non-uniform spatially varying optical signal to impinge on a portion of the medium, the first non-uniform spatially varying optical signal including a randomly distributed spatial intensity pattern;
    processing a second optical signal emitted from the medium in response to the first optical signal, including determining characteristics of a spatial variation of the second optical signal including processing the second optical signal to transform the second optical signal from a spatial representation to a spatial frequency domain representation at one or more spatial frequencies; and
    determining the one or more quantities characterizing the medium based on the characteristics of the spatial variation of the second optical signal including determining a spatial frequency response of the portion of the medium at the one or more spatial frequencies.

27. The method of claim 26 wherein the translucent medium is a biological tissue.

28. The method of claim 27 wherein the biological tissue is eye tissue.

29. The method of claim 27 wherein the biological tissue is skin tissue.

* * * * *